US010864205B2

(12) United States Patent
Damaj

(10) Patent No.: US 10,864,205 B2
(45) Date of Patent: *Dec. 15, 2020

(54) NUTRITIONAL SUPPLEMENT FOR IMPROVING SEXUAL HEALTH IN MEN AND WOMEN

(71) Applicant: Innovus Pharmaceuticals, Inc., San Diego, CA (US)

(72) Inventor: Bassam Damaj, San Diego, CA (US)

(73) Assignee: Innovus Pharmaceuticals, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/829,822

(22) Filed: Dec. 1, 2017

(65) Prior Publication Data

US 2019/0167657 A1  Jun. 6, 2019

(51) Int. Cl.
*A61K 31/198* (2006.01)
*A23L 33/175* (2016.01)
*A61P 15/10* (2006.01)
*A61K 31/4525* (2006.01)
*A61K 9/14* (2006.01)
*A61K 31/00* (2006.01)
*A61K 9/48* (2006.01)
*A23L 33/105* (2016.01)
(Continued)

(52) U.S. Cl.
CPC ........ *A61K 31/4525* (2013.01); *A23L 33/105* (2016.08); *A23L 33/16* (2016.08); *A23L 33/175* (2016.08); *A61K 9/0053* (2013.01); *A61K 9/146* (2013.01); *A61K 9/4866* (2013.01); *A61K 31/00* (2013.01); *A61K 31/198* (2013.01); *A61K 36/67* (2013.01); *A61K 47/02* (2013.01); *A61K 47/12* (2013.01); *A61K 47/38* (2013.01); *A61P 15/00* (2018.01); *A61P 15/10* (2018.01); *A23V 2002/00* (2013.01)

(58) Field of Classification Search
CPC .. A61K 31/4525; A61K 31/198; A61K 36/67; A23L 33/175; A61P 15/10; A61P 15/12
See application file for complete search history.

(56) References Cited

U.S. PATENT DOCUMENTS 5,536,506 A    7/1996  Majeed et al.
5,744,161 A *  4/1998  Majeed ................ A61K 9/0014
                                              424/423

(Continued)

FOREIGN PATENT DOCUMENTS

EP    0810868 B1    8/2001
EP    2027857 A2    2/2009
(Continued)

OTHER PUBLICATIONS

Vesele Product Insert, Innovus Pharmaceuticals, Inc., Oct. 2016. (Year: 2016).*

(Continued)

Primary Examiner — Craig D Ricci
Assistant Examiner — Janet L. Coppins
(74) Attorney, Agent, or Firm — Sheridan Ross P.C.

(57) ABSTRACT

The invention provides compositions and methods that are effective to improve NO production in vivo and/or to increase NO levels in blood. Such compositions and methods are useful to improve sexual function in males and females.

5 Claims, 3 Drawing Sheets

(51) Int. Cl.
  *A23L 33/16* (2016.01)
  *A61P 15/00* (2006.01)
  *A61K 9/00* (2006.01)
  *A61K 36/67* (2006.01)
  *A61K 47/02* (2006.01)
  *A61K 47/12* (2006.01)
  *A61K 47/38* (2006.01)

(56) References Cited

U.S. PATENT DOCUMENTS

| | | | |
|---|---|---|---|
| 7,262,192 B2 | 8/2007 | Bell et al. | |
| 9,161,565 B1 | 10/2015 | Bezzek | |
| 2001/0008641 A1 | 7/2001 | Krotzer | |
| 2008/0305096 A1 | 12/2008 | Verdegem et al. | |
| 2009/0143433 A1 | 6/2009 | Hendrix | |
| 2016/0106793 A1 | 4/2016 | Peltier et al. | |
| 2018/0325903 A1 | 11/2018 | Damaj | |

FOREIGN PATENT DOCUMENTS

| | | | |
|---|---|---|---|
| WO | 2015048590 A1 | 4/2015 | |
| WO | 2015061860 A1 | 5/2015 | |

OTHER PUBLICATIONS

Webpage pdf of "Internet Archive Wayback Machine" search for "www.recalmax.com/recalmax-insert.html" dated Jun. 19, 2017. (Year: 2017).*
Recalmax Product Insert, Innovus Pharmaceuticals, Inc., Oct. 2016. (Year: 2016).*
U.S. Appl. No. 15/979,120, US 2018-0325903.
U.S. Appl. No. 15/829,799.
U.S. Appl. No. 15/829,798.
U.S. Appl. No. 15/829,797.
U.S. Appl. No. 15/829,801.
Awad, et al., "Effect of beta-sitosterol, a plant sterol, on growth, protein phosphatase 2A, and phospholipase D in LNCaP cells", Nutr Cancer 36(1), 74-78 (2000) Abstract, 2 pages.
Fry, et al., "Impact of Nitric-oxide-mediated vasodilation and oxidative stress on renal medullary oxygenation: modeling study", Am J Physiol Renal Physiol 310, F237-F247 (2016).
Life Extension, "All About Supplements—Pygeum", http://222.lifeextension.com/magazine/2006/4/aas/page-01, 5 pages, retrieved on Sep. 24, 2018.
Manukhana, et al., "General Pathology and Pathophysiology. Role of Nitric Oxide in Prevention of Cognitive Disorders in Neurodegenerative Brain Injuries in Rats", Bulletin of Experimental Biology and Medicine 146(4), 391-395 (2008).
Mascio, et al., "Lycopene as the most efficient biological carotenoid singlet oxygen quencher", Archives of Biochemistry and Biophysics 274(2), 532-538 (1989). Abstract, 2 pages.
Mehmood, et al., "Black Pepper and Piperine Possess Antidiarrheal Effect Mediated Through Phosphodiesterase Inhibitory and CA++ Antagonist Pathways", Basic & Clinical Pharmacology & Toxicology 1 (Suppl 1) Abstract # 834, 256 (2014).
Morris, "Arginine Metabolism: Enzymology, Nutrition, and Clinical Significance. Enzymes of Arginine Metabolism", J Nutri 134, 2743S-2747S (2004).
Mukhtar, et al., "Green Tea in Chemoprevention of Cancer", Toxicological Sciences 52 (Supplement), 111-117 (1999).
NULIV Science, "ASTRAGIN", Product Insert pdf, www.nulivscience.com, 2 pages (2018).
NULIV Science, "NUTRA", http://www.nutraingredients-usa.com/articles/2012/03/26nuliv-science-annouces-self-affirmed-GRAS-for-AstraGin-ingredient, 2 pages (2012).
Perva-Uzunalic, et al., "Extraction of active ingredients from green tea (*Camellia sinensis*): Extraction efficiency of major catechins and caffeine", Food Chemistry 96, 597-605 (2006).
Puritan's Pride, "Arginine", Citrulline complex capsules from Puritan's Pride, 3 pages (2013).
Riehemann, et al., "Plant extracts from stinging nettle (*Urtica dioica*), an antirheumatic remedy, inhibit the proinflammatory transcription factor NF-kB", FEBS Letters 442, 89-94 (1999).
Simon, et al., "Decoding the Substrate Supply to Human Neuronal Nitric Oxide Synthase", PLOS One 8(7), e67707, 12 pages (2013).
U.S. Non-Final Office Action, for U.S. Appl. No. 15/829,801, 10 pages, dated Jun. 29, 2018.
U.S. Non-Final Office Action, for U.S. Appl. No. 15/829,801, 17 pages, dated Nov. 20, 2018.
WEBMD, "Saw Palmetto", https://www.webmd.com/vitamins/ai/ingredientmono-971/saw-palmetto, 4 pages, retrieved on Sep. 24, 2018.
CAS Registry, RN 94-62-2, Listing for Piperine, 1 page, (1984).

* cited by examiner

Piperine Structure (2*E*,4*E*)-5-(benzo[*d*][1,3]dioxol-5-yl)-1-(piperidin-1-yl)penta-2,4-dien-1-one

NUTRITIONAL SUPPLEMENT FOR IMPROVING SEXUAL HEALTH IN MEN AND WOMEN

BACKGROUND OF THE INVENTION

Nitric Oxide Synthase (NOS) in endothelial cells converts L-arginine to L-hydroxyarginine and subsequently to nitric oxide (NO) and L-citrulline (FIG. 1 and FIG. 2). NO mediates its biological effects by activating guanylyl cyclase and increasing cyclic GMP synthesis from GTP which leads to the regulation of several biological processes such as vasodilation. Two L-citrulline molecules combine to generate L-arginine to boost the NO generation cycle. NO exerts its biological action on smooth muscle by increasing cGMP which leads to vasodilation and increased blood flow in the genitals. A main problem with arginine based supplements is the low absorption by the human body resulting is little to now efficacy.

A previous dietary supplement was designed and sold to maximize the benefits of NO. It contained the amino acids L-citruline and L-arginine, as well as BioPerine® (extract containing piperine), a piperine (FIG. 3) extract that helps the body absorb the amino acids (see U.S. Pat. No. 5,536,506 and European Patent EP0810868B1). For men, daily consumption of the previous dietary supplement provided a significant improvement of erection hardness and maintenance, frequency of intercourse with partner and partner satisfaction as well as an overall satisfaction with sexual health resulting from the increase of nitric oxide levels in blood. Women taking the previous dietary supplement the present invention also reported a significant satisfaction in lubrication, sexual desire, ability to be aroused and frequency of intercourse with partner.

The previous dietary supplement was sold and administered as a capsule containing 500 mg of L-citrulline, 250 mg of L-arginine, and 1.25 mg of bioperine. In spite of the success realized with the previous dietary supplement, there remains a need for additional formulations that provide improved effects.

SUMMARY OF THE INVENTION

Applicant has determined that the beneficial effects of the previous dietary supplement can be significantly improved by increasing the amount of piperine in the formulation from 1.25 mg to about 5 mg. Based on the suggested administration of two capsules per day, this represents an increase in the amount of piperine from 2.5 mg to about 10 mg per day.

Accordingly, in one embodiment the invention provides a unit dosage form suitable for oral administration to a human comprising: L-citrulline (500 mg±20 mg); L-arginine (250 mg±20 mg); and at least about 5 mg piperine.

In another embodiment the invention provides a unit dosage form suitable for oral administration to a human comprising: about 500 mg of L-citrulline; about 250 mg of L-arginine; and about 5 mg of bioperine.

In another embodiment the invention provides a method to increase NO levels in the blood of a mammal comprising administering a unit dosage form of the invention to the mammal.

In another embodiment the invention provides a method to treat erectile dysfunction in a mammal comprising administering a unit dosage form of the invention to the mammal.

In another embodiment the invention provides a method to improve sexual function in a mammal comprising administering a unit dosage form of the invention to the mammal.

In another embodiment the invention provides a method to improve erection hardness, erection maintenance, frequency of intercourse, partner satisfaction, or overall satisfaction with sexual health in a male human comprising administering a unit dosage form of the invention to the male human.

In another embodiment the invention provides a method to improve lubrication, sexual desire, ability to be aroused or frequency of intercourse, in a female human comprising administering a unit dosage form of the invention to the female human.

DETAILED DESCRIPTION

Figure 1:
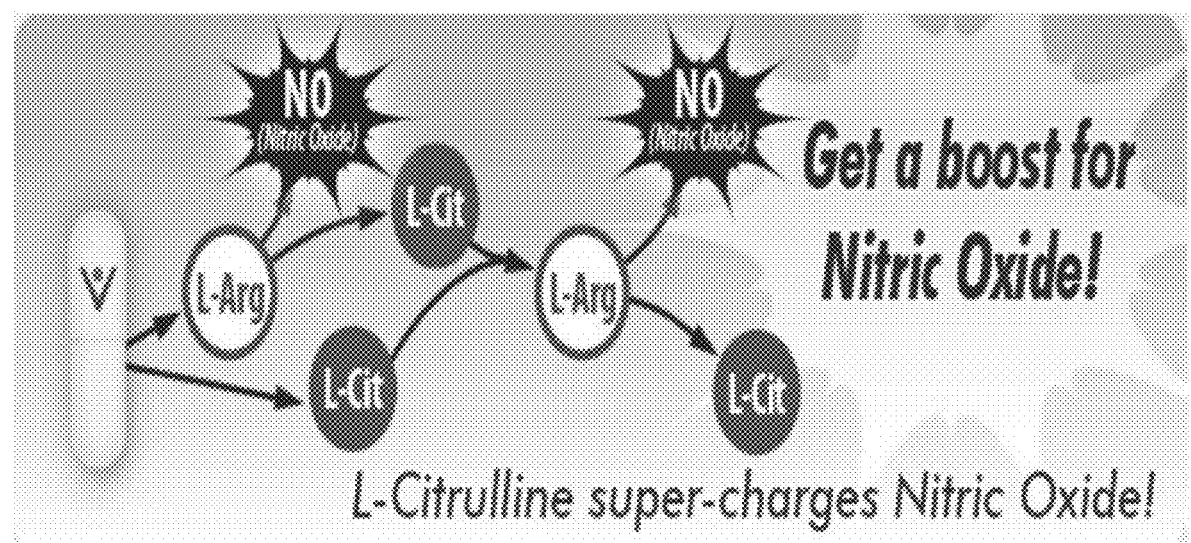
FIG. 1 shows the conversion of L-citrulline and L-arginine to NO.
Figure 2:
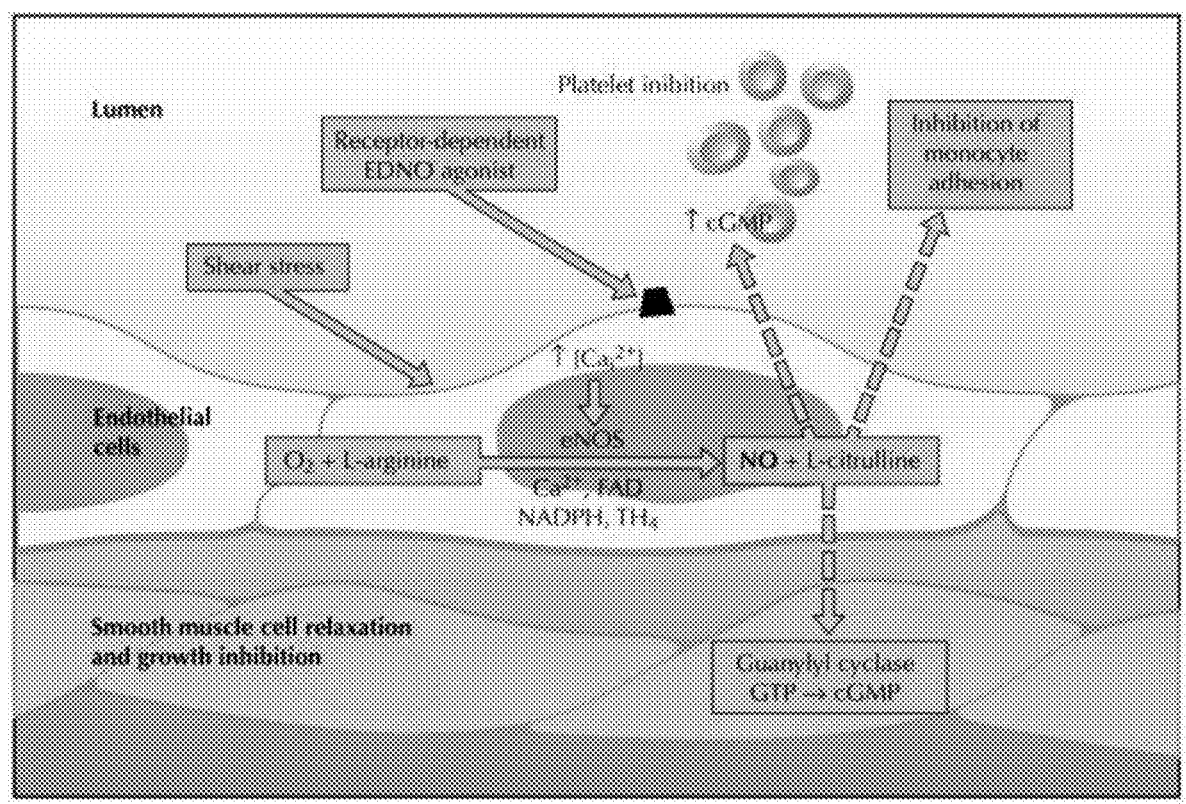
FIG. 2 shows how Nitric Oxide Synthase (NOS) in endothelial cells converts L-arginine to L-hydroxyarginine and subsequently to nitric oxide (NO) and L-citrulline.
Figure 3:
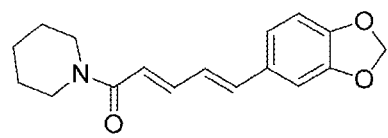
FIG. 3 shows the structure for piperine.

In one embodiment a unit dosage form of the invention may contain one or more pharmaceutical diluents or excipients. For example, in one embodiment a unit dosage form of the invention may comprise microcrystalline cellulose, silicon dioxide, and magnesium stearate. The present invention may be administered in a capsule, powder, or liquid.

In one embodiment a unit dosage form of the invention may comprise at least about 480 mg of L-citrulline.

In one embodiment a unit dosage form of the invention may comprise at least about 490 mg of L-citrulline.

In one embodiment a unit dosage form of the invention may comprise at least about 500 mg of L-citrulline.

In one embodiment a unit dosage form of the invention may comprise at least about 230 mg of L-arginine.

In one embodiment a unit dosage form of the invention may comprise at least about 240 mg of L-arginine.

In one embodiment a unit dosage form of the invention may comprise at least about 250 mg of L-arginine.

In one embodiment a unit dosage form of the invention may comprise: about 500 mg of L-citrulline; about 250 mg of L-arginine; and about 1.75 mg of bioperine.

In one embodiment the piperine is synthetically produced piperine.

In one embodiment the piperine is an extract from the fruit of Piper.

L-Argenine is an α-amino acid that is used in the biosynthesis of proteins. It is the precursor for the biosynthesis of nitric oxide. L-Argenine has the following structure:

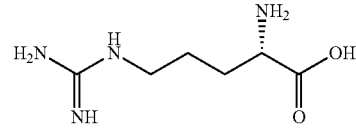 [SMILES: N=C(N)NCCC[C@H](N)C(=O)O]

In humans, arginine is classified as a semiessential or conditionally essential amino acid, depending on the developmental stage and health status of the individual. L-Argenine is commercially available from a variety of sources.

L-Citrulline is an α-amino acid that is a key intermediate in the urea cycle, the pathway by which mammals excrete ammonia by converting it into urea. Citrulline is also produced as a byproduct of the enzymatic production of nitric oxide from the amino acid arginine, catalyzed by nitric oxide synthase. L-Citrulline has the following structure:

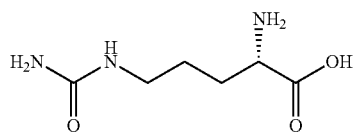 [SMILES: NC(=O)NCCC[C@H](N)C(=O)O]

L-Citrulline is commercially available from a variety of sources.

Bioperine® is a patented absorption enhancer, obtained from black pepper fruits (*Piper nigrum*). Bioperine® helps the body absorb the amino acids (see U.S. Pat. No. 5,536,506 and European Patent EP0810868B1). BioPerine® (extract) inhibits human CYP3A4 and P-glycoprotein enzymes. By inhibiting certain enzymes BioPerine® (extract) may alter the effectiveness of certain medications by increasing bioavailability. Bioperine is Generally Recognized As Safe (GRAS). Bioperine® (CAS Reg. No. 94-62-2) is named as 1-piperylpiperidine; 5-(1,3-benzodioxol-5-yl)-1-(piperidin-1-yl)penta-2,4-dien-1-one; and (2E,4E)-5-(1,3-benzodioxol-5-yl)-1-(piperidin-1-yl)penta-2,4-dien-1-one, and has the structure:

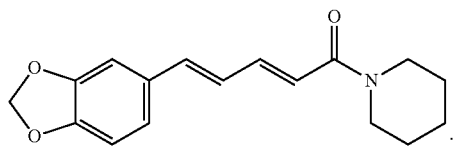 [SMILES: O=C(/C=C/C=C/c1ccc2c(c1)OCO2)N1CCCCC1]

1-Piperylpiperidine is commercially available from a variety of sources.

The invention will now be illustrated by the following non-limiting Examples.

Example 1

The chart below describes the changes between the old formulation and the present invention based on the customer satisfaction rate for the customer's ability to be aroused. The new formulation shows a 27 percent increase in ability to be aroused as opposed to the old formulation with only as 12.9 percent increase in ability to be aroused.

| Timeline | Old Formulation Satisfaction Rate | Present Invention satisfaction rate |
| --- | --- | --- |
| Baseline | 59.4 | 53.6 |
| At 4 Month | 72.3 | 80.6 |
| % Increase | 12.9 | 27 |

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A unit dosage form suitable for oral administration to a human comprising:
   about 500 mg of L-citrulline;
   about 250 mg of L-arginine; and
   from 1.75 mg to 5 mg piperine.

2. The unit dosage form of claim 1 that further comprises microcrystalline cellulose, silicon dioxide, and magnesium stearate.

3. The unit dosage form of claim 1 wherein the piperine is synthetically produced piperine.

4. The unit dosage form of claim 1 wherein the piperine is an extract from the fruit of Piper.

5. The unit dosage form of claim 1 that is formulated as a powder or liquid.

* * * * *